(12) United States Patent
Motomura et al.

(10) Patent No.: US 9,897,528 B2
(45) Date of Patent: Feb. 20, 2018

(54) PARTICULATE DETECTION SYSTEM

(71) Applicant: NGK SPARK PLUG CO., LTD., Nagoya-shi, Aichi (JP)

(72) Inventors: Masayuki Motomura, Komaki (JP); Takeshi Sugiyama, Ichinomiya (JP); Kazunari Kokubo, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 0 days.

(21) Appl. No.: 14/911,363

(22) PCT Filed: Jun. 27, 2014

(86) PCT No.: PCT/JP2014/003439
§ 371 (c)(1),
(2) Date: Feb. 10, 2016

(87) PCT Pub. No.: WO2015/025450
PCT Pub. Date: Feb. 26, 2015

(65) Prior Publication Data
US 2016/0202167 A1    Jul. 14, 2016

(30) Foreign Application Priority Data
Aug. 21, 2013  (JP) ................. 2013-171122

(51) Int. Cl.
*G01N 15/06* (2006.01)
*F01N 9/00* (2006.01)
(Continued)

(52) U.S. Cl.
CPC ......... *G01N 15/0656* (2013.01); *F01N 9/002* (2013.01); *F01N 11/00* (2013.01); *G01N 2015/0046* (2013.01)

(58) Field of Classification Search
CPC ..... F01N 11/00; F01N 9/002; G01N 15/0656; G01N 2015/0046
See application file for complete search history.

(56) References Cited

U.S. PATENT DOCUMENTS 4,656,832 A    4/1987  Yukihisa et al.
5,147,423 A *  9/1992  Richards .................. B03C 3/38
                                              96/62
(Continued)

FOREIGN PATENT DOCUMENTS

JP    59-196453 A    11/1984
JP    63068867 A *    3/1988
(Continued)

OTHER PUBLICATIONS

Search Report dated Sep. 16, 2014 by the International Searching Authority in related Application No. PCT/JP2014/003439 (PCT/ISA/210).
(Continued)

Primary Examiner — Harshad R Patel
Assistant Examiner — Punam Roy
(74) Attorney, Agent, or Firm — Sughrue Mion, PLLC (57) ABSTRACT

A particulate detection system (1) for detecting the quantity of particulates S in a gas under measurement EG includes first heater energization means S2 to S3, current convergence determination means S4 to S5, S7 to S8, second heater energization means S6, and detection start means S10. S2 to S3 performs low-temperature energization of heater (78) for a predetermined period after operation of ion source (11) is started by ion source drive circuit (210) such that gaseous discharge current Id becomes equal to a predetermined target current It. S4 to S5, S7 to S8 determines, after elapse of the predetermined period, whether or not Id has converged to an allowable range IR. When S4 to S5 determines that Id has not yet converged, S6 performs high-temperature energiza-
(Continued)

tion of the heater (78) until Id converges. Then, S10 starts detection of particulates S using signal Is detected by a detection circuit (230).

2 Claims, 8 Drawing Sheets

(51) Int. Cl.
*F01N 11/00* (2006.01)
*G01N 15/00* (2006.01)

(56) References Cited

U.S. PATENT DOCUMENTS

| | | | | |
|---|---|---|---|---|
| 6,902,604 | B2* | 6/2005 | Heckel | B03C 3/49 55/385.3 |
| 8,652,240 | B2* | 2/2014 | Sugiyama | G01N 1/2252 60/275 |
| 9,476,807 | B2* | 10/2016 | Motomura | G01N 15/0656 |
| 2010/0000404 | A1* | 1/2010 | Sakuma | G01N 15/0656 95/3 |
| 2010/0000863 | A1* | 1/2010 | Kondo | G01N 15/0656 204/406 |
| 2010/0229724 | A1* | 9/2010 | Tokuda | G01N 15/0656 96/19 |
| 2011/0050243 | A1 | 3/2011 | Tikkanen | |
| 2012/0260636 | A1 | 10/2012 | Hashida et al. | |
| 2012/0285219 | A1 | 11/2012 | Matuoka et al. | |
| 2014/0352405 | A1* | 12/2014 | Motomura | G01N 15/0656 73/23.31 |
| 2015/0204759 | A1* | 7/2015 | Sugiyama | G01N 15/0656 73/114.71 |
| 2016/0011093 | A1* | 1/2016 | Matsuoka | G01N 15/0656 73/23.33 |
| 2016/0195463 | A1* | 7/2016 | Motomura | G01N 15/0656 73/23.31 |

FOREIGN PATENT DOCUMENTS

| | | | | |
|---|---|---|---|---|
| JP | 02130568 | A * | 5/1990 | B41J 2/415 |
| JP | 2011-33577 | A | 2/2011 | |
| JP | 2011-513742 | A | 4/2011 | |
| JP | 2012-194077 | A | 10/2012 | |
| JP | 2012-237641 | A | 12/2012 | |
| WO | 2012/114518 | A1 | 8/2012 | |

OTHER PUBLICATIONS

Watanabe et al., "Measurement of the Soot and Dust Discharged from Incinerators and Industry Plants", Transactions of the Society of Instrument and Control Engineers, vol. 35, No. 10, Oct. 30, 1999, 8 total pages.

Lee et al., "Application and performance test of a micro-machined unipolar charger for real-time measurements of exhaust particles from a diesel engine vehicle", Journal of Aerosol Science, vol. 42, No. 11, Nov. 2011, 12 total pages.

* cited by examiner

PARTICULATE DETECTION SYSTEM

TECHNICAL FIELD

The present invention relates to a particulate detection system for detecting the quantity of particulates contained in a gas under measurement which flows through a gas flow pipe.

BACKGROUND ART

Exhaust gas discharged from an internal combustion engine (for example, a diesel engine or a gasoline engine) may contain particulates such as soot.

Exhaust gas containing such particulates is purified by means of collecting the particulates through use of a filter. Therefore, if the filter suffers breakage or a like failure, unpurified exhaust gas is discharged directly to the downstream side of the filter.

Therefore, there has been demanded a particulate detection system which can detect the quantity of particulates contained in exhaust gas in order to directly measure the quantity of particulates contained in exhaust gas or to detect a failure of the filter.

For example, Patent Document 1 discloses a particulate measurement method and apparatus. In the method disclosed in Patent Document 1, clean gas is ionized by means of corona discharge, the ionized gas containing positive ions is mixed with exhaust gas which is introduced from an exhaust pipe into a channel and which contains particulates, so as to electrify the particulates, and the particulates are then released to the exhaust pipe. A current (signal current) which flows in accordance with the quantity of the released, electrified particulates is detected so as to detect the particulate concentration.

Also, Patent Document 2 discloses a concrete structure of a particulate sensor which uses such ions generated by means of corona discharge. As disclosed in Patent Document 2, a constant current circuit is generally used as a power supply circuit for supplying electrical power for corona discharge, and when corona discharge is to be produced, constant current of, for example, about 5 µA is supplied to an electrode for corona discharge.

PRIOR ART DOCUMENTS

Patent Documents

Patent Document 1: Japanese Kohyo (PCT) Patent Publication No. 2011-513742
Patent Document 2: Japanese Patent Application Laid-Open (kokai) No. 2012-194077

SUMMARY OF THE INVENTION

Problems to be Solved by the Invention

Incidentally, in order to accurately detect the quantity of particulates, the current (e.g., 5 µA) controlled by the above-mentioned constant current circuit must be stable at a fixed level. However, in many cases, the current supplied for corona discharge is unstable immediately after the start of corona discharge. In particular, when the insulation properties of an ion source have deteriorated due to adhesion of water (e.g., condensed water) or a foreign substance other than water (e.g., soot) to the circumference of the ion source, that current may fail to converge to a predetermined value in some cases. In such a state, the quantity of ions generated by means of corona discharge varies. Therefore, if the quantity of particulates is detected in the state in which the current is unstable, difficulty is encountered in accurately detecting the quantity of particulates.

The present invention has been accomplished in view of such a problem, and its object is to provide a particulate detection system which can accurately detect the quantity of particulates by preventing the detection from being performed in a state in which detection accuracy has dropped due to adhesion of water or a foreign substance to the circumference of an ion source.

Means for Solving the Problems

One mode of the present invention is a particulate detection system for detecting the quantity of particulates contained in a gas under measurement flowing through a gas flow pipe. The particulate detection system comprises a detection section attached to the gas flow pipe, a drive circuit for driving the detection section, and a control section for controlling the drive circuit and detecting the quantity of the particulates. The detection section includes an ion source for generating ions by means of gaseous discharge, a particulate electrification section for mixing a portion of the gas under measurement with the ions to thereby produce electrified particulates which originate from the particulates within the gas under measurement and which carry the ions adhering thereto, and a heater for heating the ion source. The drive circuit includes an ion source drive circuit for performing constant current control such that the gaseous discharge current supplied to the ion source becomes equal to a predetermined target current, and a heater energization circuit for energizing the heater. The control section includes a detection circuit for detecting a signal corresponding to the quantity of the electrified particulates, first heater energization means for causing the heater energization circuit to perform low-temperature energization for a predetermined period after operation of the ion source by the ion source drive circuit has been started, to thereby increase the temperature of the heater to a heater temperature at which water adhering to the ion source is removed, current convergence determination means for determining, after elapse of the predetermined period, whether or not the gaseous discharge current supplied from the ion source drive circuit has converged to a predetermined allowable range including the target current, second heater energization means, operable when the current convergence determination means determines that the gaseous discharge current has not yet converged, for causing the heater energization circuit to perform high-temperature energization until the gaseous discharge current converges to the predetermined allowable range, to thereby increase the temperature of the heater to a heater temperature at which a foreign substance which adheres to the ion source and cannot be removed by the low-temperature energization is removed, and detection start means for starting detection of the quantity of the particulates through use of the signal after the gaseous discharge current has converged to the allowable range.

In this particulate detection system, the ion source drive circuit performs constant current control such that the gaseous discharge current supplied to the ion source becomes equal to the predetermined target current.

However, as described above, the gaseous discharge current is unstable immediately after the operation of the ion source by the ion source drive circuit has been started. Also, when the insulation properties of the ion source have deteriorated due to adhesion of condensed water or soot to the circumference of the ion source, the gaseous discharge current may take a great deal of time to converge to the target current. In such a state where the gaseous discharge current is unstable, the quantity of the generated ions varies. Therefore, difficulty is encountered in accurately detecting the quantity of particulates through use of a signal detected by the detection circuit and corresponding to the quantity of electrified particulates (for example, a current which flows in accordance with the quantity of electrified particulates).

In view of the foregoing problem, in this particulate detection system, the first heater energization means causes the heater energization circuit to perform low-temperature energization for a predetermined period after the operation of the ion source has been started, to thereby increase the temperature of the heater to a heater temperature (for example, 100 to 200° C.) at which water adhering to the ion source is removed.

In the case where the gaseous discharge current has not converged to the allowable range despite of elapse of the predetermined period, the second heater energization means causes the heater energization circuit to perform high-temperature energization until the gaseous discharge current converges to the allowable range, to thereby increase the temperature of the heater to a heater temperature (for example, 600° C.) at which a foreign substance (other than water) which adheres to the ion source and which cannot be removed by the low-temperature energization is removed.

Namely, at the beginning, the heater is energized by the low-temperature energization so as to remove water adhering to the ion source. However, in the case where the gaseous discharge current has not converged to the allowable range despite of elapse of the predetermined period, the heater is energized by the high-temperature energization so as to remove a foreign substance adhering to the ion source. Notably, examples of the foreign substance which cannot be removed by the low temperature energization include soot and oil flowing through the gas flow pipe.

Therefore, the amount of current consumed as a result of the energization of the heater at the beginning can be reduced by the low-temperature energization performed by the first heater energization means. In addition, when necessary, the heater is energized by the high-temperature energization performed by the second heater energization means such that its temperature increases to a temperature at which a foreign substance (e.g., soot) which adheres to the ion source and which cannot be removed by the low-temperature energization is removed, whereby the heat source is heated. Thus, the gaseous discharge current can be caused to converge to the allowable range.

Since the detection of the quantity of the particulates through use of the signal is started in a state in which the gaseous discharge is stable, the detection is not performed in a state in which the detection accuracy has dropped. Therefore, the quantity of the generated ions becomes stable, and the quantity of the particulates can be detected accurately. Also, it is possible to remove water droplets (e.g., droplets of condensed water) and foreign substances (e.g., soot), which adhere to the circumference of the ion source, to thereby recover the insulation properties of the ion source. Thus, the gaseous discharge current can be quickly converged to the allowable range, whereby the time required to start the detection of the quantity of the particulates can be shortened.

Notably, as described above, an example of the signal detected by the detection circuit and corresponding to the quantity of electrified particulates is a current corresponding to the quantity of electrified particulates. Also, an example of a method of detecting the quantity of electrified particulates through use of the signal detected by the detection circuit is a method of converting the detected signal (current) to the quantity of electrified particulates by using a predetermined conversion equation or a predetermined reference table. Also, the magnitude of the current detected by the detection circuit may be used as a physical quantity corresponding to the quantity of electrified particulates, without performing such conversion.

Further, in any of the above-described particulate detection systems, preferably, the detection section includes a collection electrode for collecting floating ions which are a portion of the ions and which failed to adhere to the particulates when the ions was mixed with the gas under measurement, and an auxiliary electrode for assisting the collection of the floating ions by the collection electrode; the drive circuit includes an auxiliary electrode drive circuit for driving the auxiliary electrode; and the heater is configured to heat the auxiliary electrode in addition to the ion source.

In this particulate detection system, an auxiliary electrode is provided, and the heater heats the auxiliary electrode in addition to the ion source. By virtue of this configuration, it is possible to recover the insulation properties of the auxiliary electrode having deteriorated as a result of adhesion of foreign substances, such as condensed water and soot, to the auxiliary electrode. Therefore, the quantity of particulates can be detected more properly.

MODE FOR CARRYING OUT THE INVENTION

Figure 1:
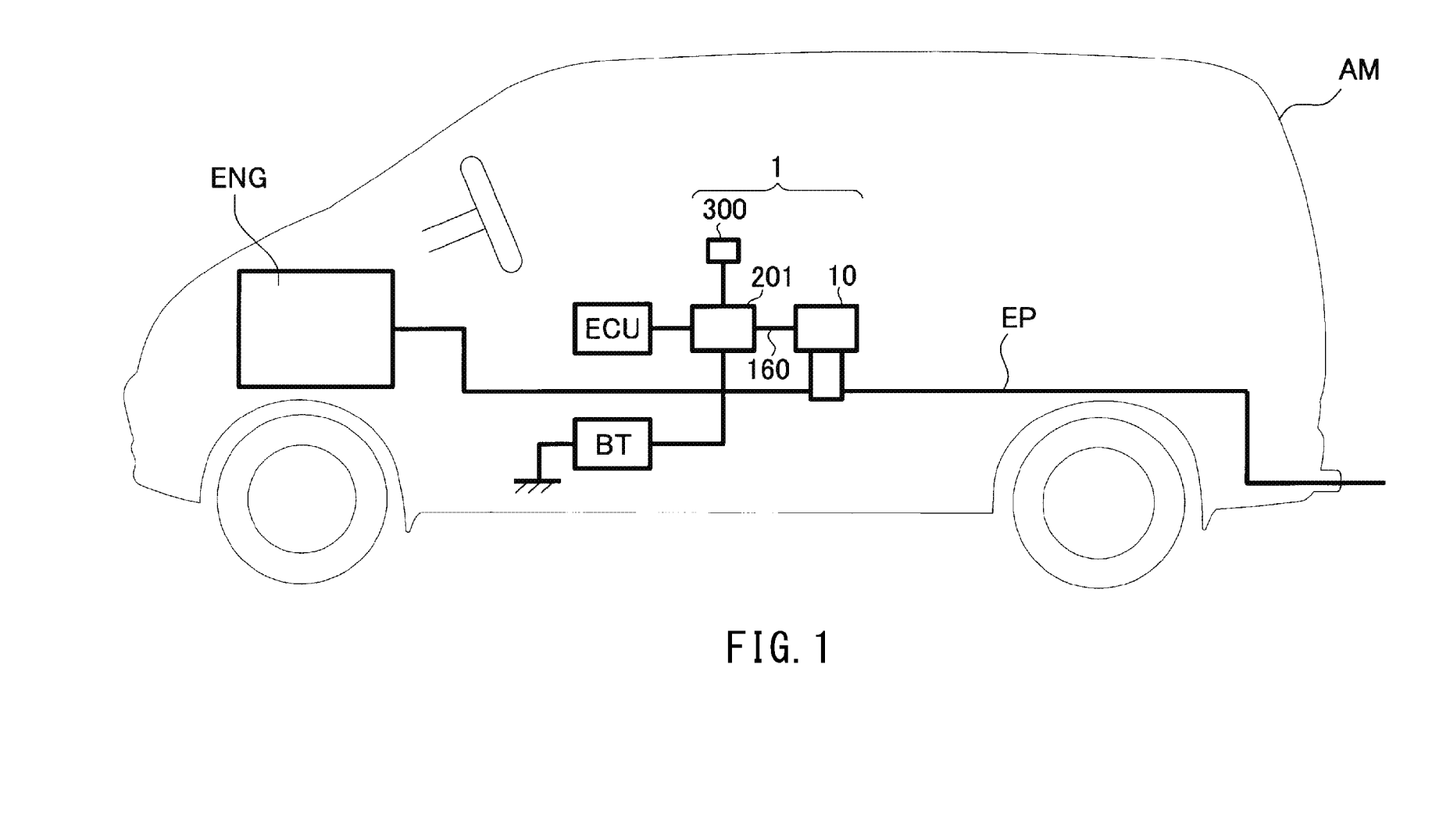
FIG. 1 Explanatory view showing a particulate detection system according to an embodiment which is applied to an exhaust pipe of an engine mounted on a vehicle.

A particulate detection system 1 according to the present embodiment will be described with reference to the drawings. The particulate detection system 1 of the present embodiment is attached to an exhaust pipe EP of an engine ENG (internal combustion engine) mounted on a vehicle AM, and detects the quantity of particulates S (soot, etc.) contained in exhaust gas EG flowing through the exhaust pipe EP (see FIG. 1). This system 1 is mainly composed of a detection section 10, a circuit section 201, and a feed pump 300 which is a compressed air source for producing compressed air AK (see FIG. 2).

The detection section 10 is attached to a mount portion EPT of the exhaust pipe EP (a gas flow pipe) where a mount opening EPO is formed. A portion of the detection section 10 (located on the right side (the distal end side) of the mount portion EPT in FIG. 2) extends into the interior of the exhaust pipe EP through the mount opening EPO and is to come into contact with the exhaust gas EG (a gas under measurement).

Outside the exhaust pipe EP, the circuit section 201 is connected to the detection section 10 through a cable 160 composed of a plurality of wires. This circuit section 201 includes a circuit which drives the detection section 10 and detects a signal current Is which will be described later.

First, the electrical configuration of the circuit section 201 of the present system 1 will be described. The circuit section 201 has a measurement control circuit 220 which includes a signal current detection circuit 230 and a heater energization circuit 226; an ion source power supply circuit 210; and an auxiliary electrode power supply circuit 240.

The ion source power supply circuit 210 has a first output terminal 211 maintained at a first potential PV1 and a second output terminal 212 maintained at a second potential PV2. Specifically, the second potential PV2 is maintained at a positive high potential in relation to the first potential PV1. More specifically, a pulse voltage (1 to 2 kV0-p) which is positive in relation to the first potential PV1 is output from the second output terminal 212. The pulse voltage is obtained through half-wave rectification of a sinusoidal wave of about 100 kHz. Notably, the ion source power supply circuit 210 constitutes a constant-current power supply whose output current is feedback-controlled by a microprocessor 202, which will be described later, such that the output current (rms or effective value) is maintained at a predetermined current value (for example, 5 $\mu$A). The microprocessor 202 can detect, through an unillustrated isolation amplifier circuit, the magnitude of the output current (discharge current Id to be described later) supplied by the ion source power supply circuit 210.

Meanwhile, the auxiliary electrode power supply circuit 240 has an auxiliary first output terminal 241 which electrically communicates with the first output terminal 211 and is maintained at the first potential PV1, and an auxiliary second output terminal 242 which is maintained at a third potential PV3. Specifically, the third potential PV3 is set to a potential of, for example, DC 100 to 200 V which is a positive high DC potential in relation to the first potential PV1 but is lower than the peak potential (1 to 2 kV) of the second potential PV2.

Moreover, the signal current detection circuit 230, which partially constitutes the measurement control circuit 220, has a signal input terminal 231 connected to the first output terminal 211 of the ion source power supply circuit 210, and a ground input terminal 232 connected to a ground potential PVE. This signal current detection circuit 230 detects the signal current Is flowing between the signal input terminal 231 and the ground input terminal 232.

Also, the heater energization circuit 226 is a circuit for energizing a heater 78 (which will be described later) through PWM control, to thereby cause the heater 78 to generate heat. The heater energization circuit 226 is connected to a first heater connection wiring line 169a and a second heater connection wiring line 169b of the cable 160.

In addition, the first output terminal 211 of the ion source power supply circuit 210, the auxiliary first output terminal 241 of the auxiliary electrode power supply circuit 240, and the signal input terminal 231 of the signal current detection circuit 230 are connected to one another.

A primary-side core 271A of an isolation transformer 270 electrically communicates with the ground potential PVE, and a secondary-side core 271B thereof electrically communicates with the first potential PV1 (the first output terminal 211 of the ion source power supply circuit 210). In the present embodiment, the measurement control circuit 220, the ion source power supply circuit 210, and the auxiliary electrode power supply circuit 240 are isolated from one another by the isolation transformer 270.

The measurement control circuit 220 includes a regulator power supply PS. This regulator power supply PS is driven by an external battery BT through a power supply wiring line BC.

Also, the measurement control circuit 220 includes the microprocessor 202, and can communicate, through a communication line CC, with a control unit ECU which controls the internal combustion engine. Thus, the measurement control circuit 220 can transmit to the control unit ECU, for example, a reduced or converted value of the quantity of particulates S which corresponds to the magnitude of the signal current Is detected by the signal current detection circuit 230.

The feed pump 300 takes in atmosphere (air) around the feed pump 300, and feeds clean, compressed air AK toward an ion source 11, which will be described later, through an air feed pipe 310.

Next, the cable 160 will be described (see FIG. 2). A second potential wiring line 161, an auxiliary potential wiring line 162, the first heater connection wiring line 169a, and the second heater connection wiring line 169b, which are formed of copper wire, and a hollow air pipe 163 formed of resin are disposed at the center of the cable 160. These wiring lines and pipe are circumferentially surrounded by a first potential wiring line 165 and a ground potential wiring line 167, each formed of braided thin copper wires, with an unillustrated insulator layer disposed therebetween.

Figure 2:
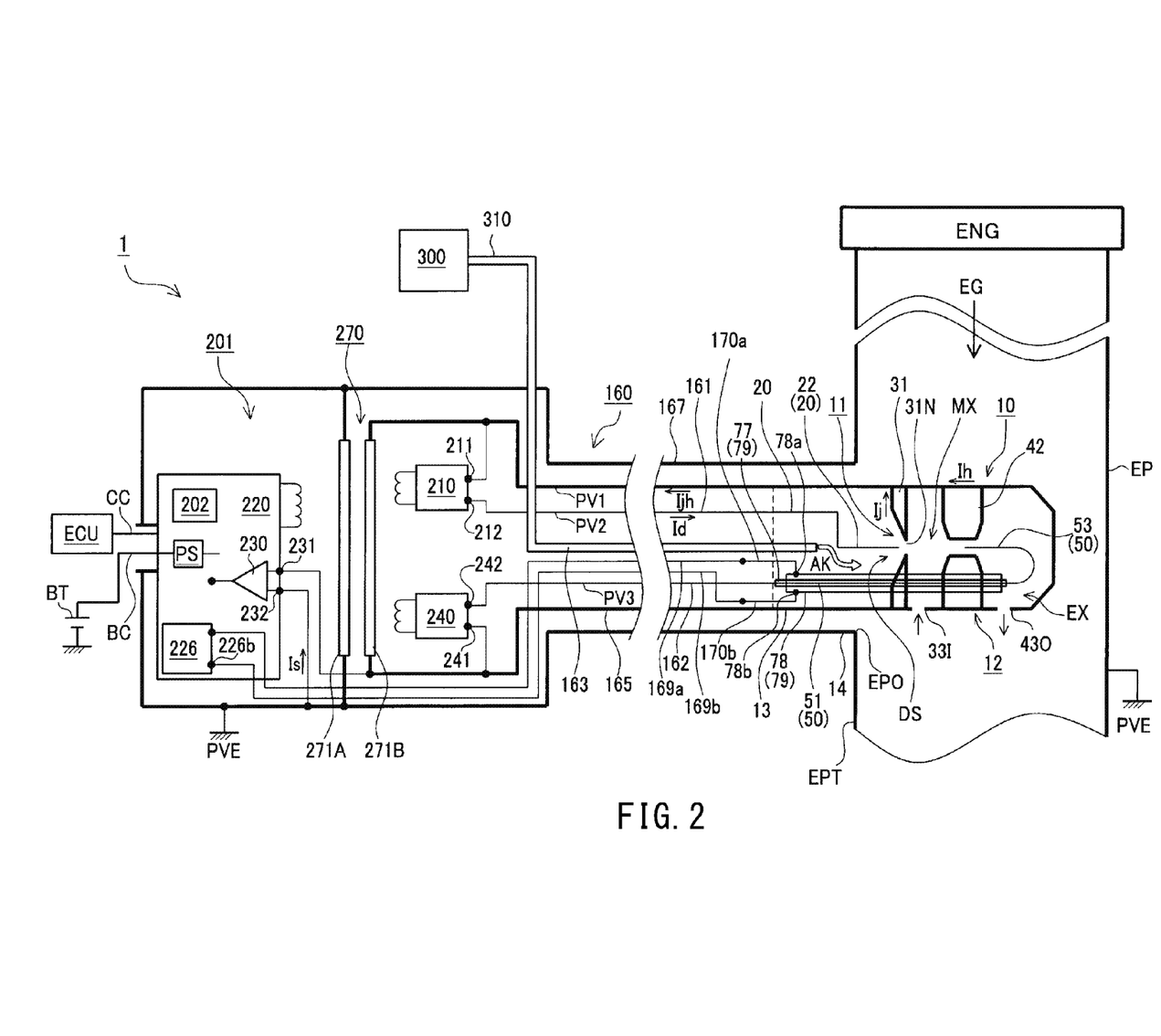
FIG. 2 Explanatory view schematically showing the configuration of the particulate detection system according to the embodiment.

As described above, the circuit section 201 is connected to this cable 160 (see FIG. 2). Specifically, the second output terminal 212 of the ion source power supply circuit 210 is maintained at the second potential PV2, and is connected to the second potential wiring line 161 so as to electrically communicate therewith. The auxiliary second output terminal 242 of the auxiliary electrode power supply circuit 240 is maintained at the third potential PV3, and is connected to the auxiliary potential wiring line 162 so as to electrically communicate therewith. The first output terminal 211 of the ion source power supply circuit 210 is maintained at the first potential PV1, and is connected to the first potential wiring line 165 so as to electrically communicate therewith. The ground input terminal 232 of the signal current detection circuit 230 is connected, for electrical communication, to the ground potential wiring line 167, whereby the ground input terminal 232 is maintained at the ground potential PVE. The heater energization circuit 226 is connected, for electrical communication, to the first heater connection wiring line 169a and the second heater connection wiring line 169b. The air feed pipe 310 is connected to the air pipe 163 of the cable 160.

Next, the detection section 10 will be described (see FIG. 2). As described above, the detection section 10 is attached to the mount portion EPT of the exhaust pipe EP (gas flow pipe) of the engine ENG (internal combustion engine), the mount portion EPT having the mount opening EPO, and is to come into contact with the exhaust gas EG (gas under measurement). From the viewpoint of the electrical functions of the detection section 10, the detection section 10 is mainly composed of an ion source 11, a particulate electrification section 12, a first conduction member 13, a needlelike electrode member 20, and an auxiliary electrode member 50.

The first conduction member 13, which is formed of metal and has a circular cylindrical shape, is connected to the first potential wiring line 165 at the distal end side of the cable 160, and electrically communicates with the first potential wiring line 165.

A distal end portion of the second potential wiring line 161 of the cable 160 is connected to the needlelike electrode member 20 inside the first conduction member 13. The needlelike electrode member 20 is formed of tungsten wire, and has a needlelike distal end portion 22 having a sharp tip end. This needlelike distal end portion 22 serves as one of the two electrodes of the ion source 11, which will be described later.

Figure 4:
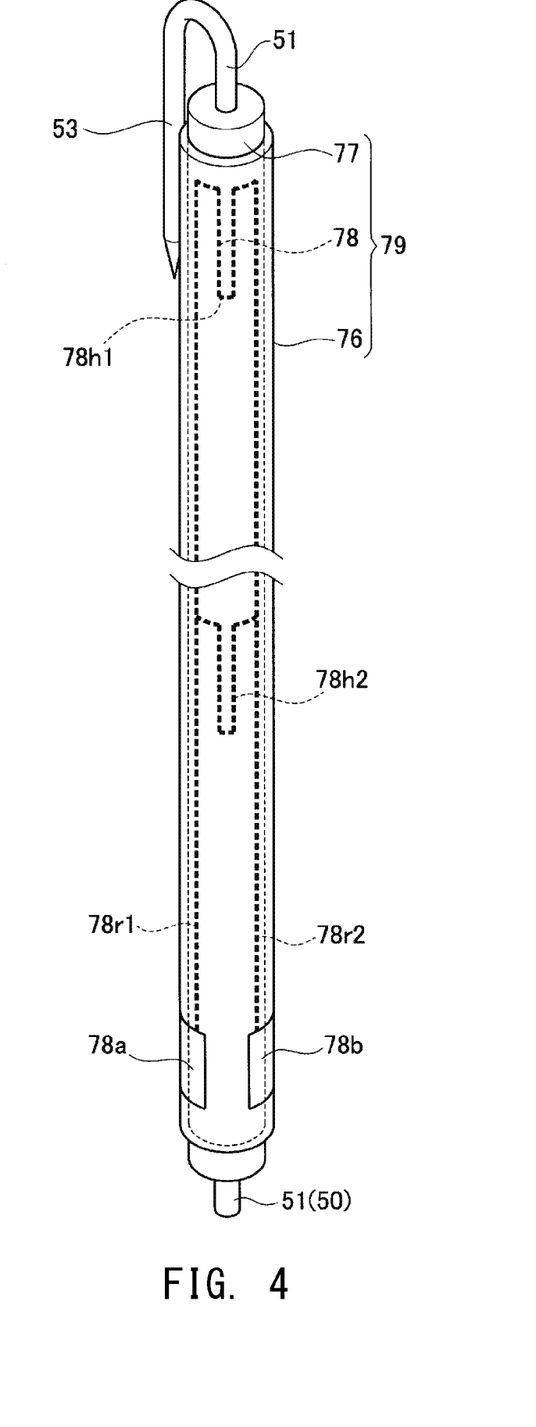
FIG. 4 Explanatory view of a portion of the particulate detection system according to the embodiment; i.e., an auxiliary electrode member and an auxiliary electrode insulating pipe with a heater which covers the auxiliary electrode member.

Also, a distal end portion of the auxiliary potential wiring line 162 of the cable 160 is connected to an extending portion 51 of the auxiliary electrode member 50 inside the first conduction member 13. The auxiliary electrode member 50 is formed of stainless steel wire, a distal end portion of the auxiliary electrode member 50 is bent back to have a U-like shape, and the auxiliary electrode member 50 has an auxiliary electrode portion 53 at a distal end portion of the bent back portion. The auxiliary electrode portion 53 serves as an auxiliary electrode which will be described later. The extending portion 51 of the auxiliary electrode member 50 is covered by an auxiliary electrode insulating pipe 79 with a heater (see FIG. 4). The heater-equipped auxiliary electrode insulating pipe 79 is composed of a cylindrical tubular, auxiliary electrode insulating pipe 77 formed of insulating ceramic such as alumina, the heater 78 formed on the surface of the auxiliary electrode insulating pipe 77 and united therewith, and an insulating ceramic layer 76 covering them.

The heater-equipped auxiliary electrode insulating pipe 79 has two heater terminals 78$a$ and 78$b$ of the heater 78 which are exposed to the outside at the proximal end side (the lower side in FIG. 4) of the insulating pipe 79. The heater 78 is formed of tungsten, and has heater lead portions 78$r$1 and 78$r$2 extending from the heater terminals 78$a$ and 78$b$ toward the distal end side (the upper side in FIG. 4), and two heating portions; i.e., a first heater portion 78$h$1 located at the distal end and a second heater portion 78$h$2 located on the proximal end side in relation to the first heater portion 78$h$1. The first heater portion 78$h$1 and the second heater portion 78$h$2 are connected in parallel. The first heater portion 78$h$1 heats the vicinity of the auxiliary electrode portion 53 of the auxiliary electrode member 50, which serves as an auxiliary electrode. The second heater portion 78$h$2 heats the vicinity of the ion source 11 (a nozzle member 31, which will be described later, and the needlelike distal end portion 22 of the needlelike electrode member 20). Namely, the heater 78 heats the ion source 11 and the auxiliary electrode portion 53 (auxiliary electrode) of the auxiliary electrode member 50 by the first heater portion 78$h$1 and the second heater portion 78$h$2, respectively.

The first conduction member 13 electrically communicates with the first output terminal 211 of the ion source power supply circuit 210 through the first potential wiring line 165 of the cable 160, whereby the first conduction member 13 is maintained at the first potential PV1. Also, the first conduction member 13 circumferentially surrounds a portion of the needlelike electrode member 20 and a portion of the auxiliary electrode member 50, which portions are located outside the exhaust pipe EP.

Further, the circumference of the first conduction member 13 is surrounded by a housing member 14 in such a manner that the first conduction member 13 is insulated from the housing member 14. The housing member 14 is attached to the exhaust pipe EP and electrically communicates therewith. The housing member 14 is connected to the cable 160 such that the housing member 14 electrically communicates with the ground potential wiring line 167 of the cable 160 and is maintained at the ground potential PVE.

The first heater connection wiring line 169$a$ and the second heater connection wiring line 169$b$ of the cable 160 are connected to heater connection terminals 170$a$ and 170$b$, respectively, inside the first conduction member 13. The heater connection terminals 170$a$ and 170$b$ are connected to the heater terminals 78$a$ and 78$b$ of the heater 78 inside the first conduction member 13.

A distal end of the air pipe 163 of the cable 160 is opened inside the first conduction member 13. The compressed air AK supplied from the feed pump 300 through the air feed pipe 310 and the air pipe 163 of the cable 160 is discharged from the air pipe 163, and is fed under pressure to a discharge space DS (which will be described later) located on the distal end side (right side in FIG. 2) of the air pipe 163.

The nozzle member 31 is fitted to a distal end portion (a right end portion in FIG. 2) of the first conduction member 13. A central portion of the nozzle member 31 is concaved toward the distal end side, and a small through hole is formed at the center. The through hole serves as a nozzle 31N. The nozzle member 31 electrically communicates with the first conduction member 13, and is maintained at the first potential PV1.

As a result of the nozzle member 31 being fitted to the distal end of the first conduction member 13, the discharge space DS is formed inside these members. In this discharge space DS, the projecting needlelike distal end portion 22 of the needlelike electrode member 20 faces a facing surface 31T which is a surface of the nozzle member 31 on the proximal end side and which has a concave shape. Accordingly, when a high voltage is applied between the needlelike distal end portion 22 and the nozzle member 31 (facing surface 31T), gaseous discharge occurs, whereby $N_2$, $O_2$, etc. in the atmosphere are ionized, whereby positive ions (e.g., $N^{3+}$, $O^{2+}$; hereinafter also referred to as "ions CP") are produced. The compressed air AK discharged from the air pipe 163 of the cable 160 is also supplied to the discharge space DS. Therefore, air AR originating from the compressed air AK is jetted at high speed from the nozzle 31N of the nozzle member 31 toward a mixing region MX (which will be described later) located on the distal end side of the nozzle 31N, and the ions CP are also jetted toward the mixing region MX together with the compressed air AK (air AR).

The particulate electrification section 12 is formed on the distal end side (on the right side in FIG. 2) of the nozzle member 31. An intake port 331 and an exhaust port 430, which are open toward the downstream side of the exhaust pipe EP) are formed in the side wall of the particulate electrification section 12. This particulate electrification section 12 communicates with the nozzle member 31 electrically as well. Therefore, the particulate electrification section 12 is maintained at the first potential PV1.

The inner space of the particulate electrification section 12 is narrowed by a collection electrode 42 which bulges inward, whereby a slit-shaped internal space is formed. As a result, on the proximal end side (on the left side in FIG. 2) of the collection electrode 42, a circular columnar space is formed between the nozzle member 31 and the collection electrode 42.

Figure 3:
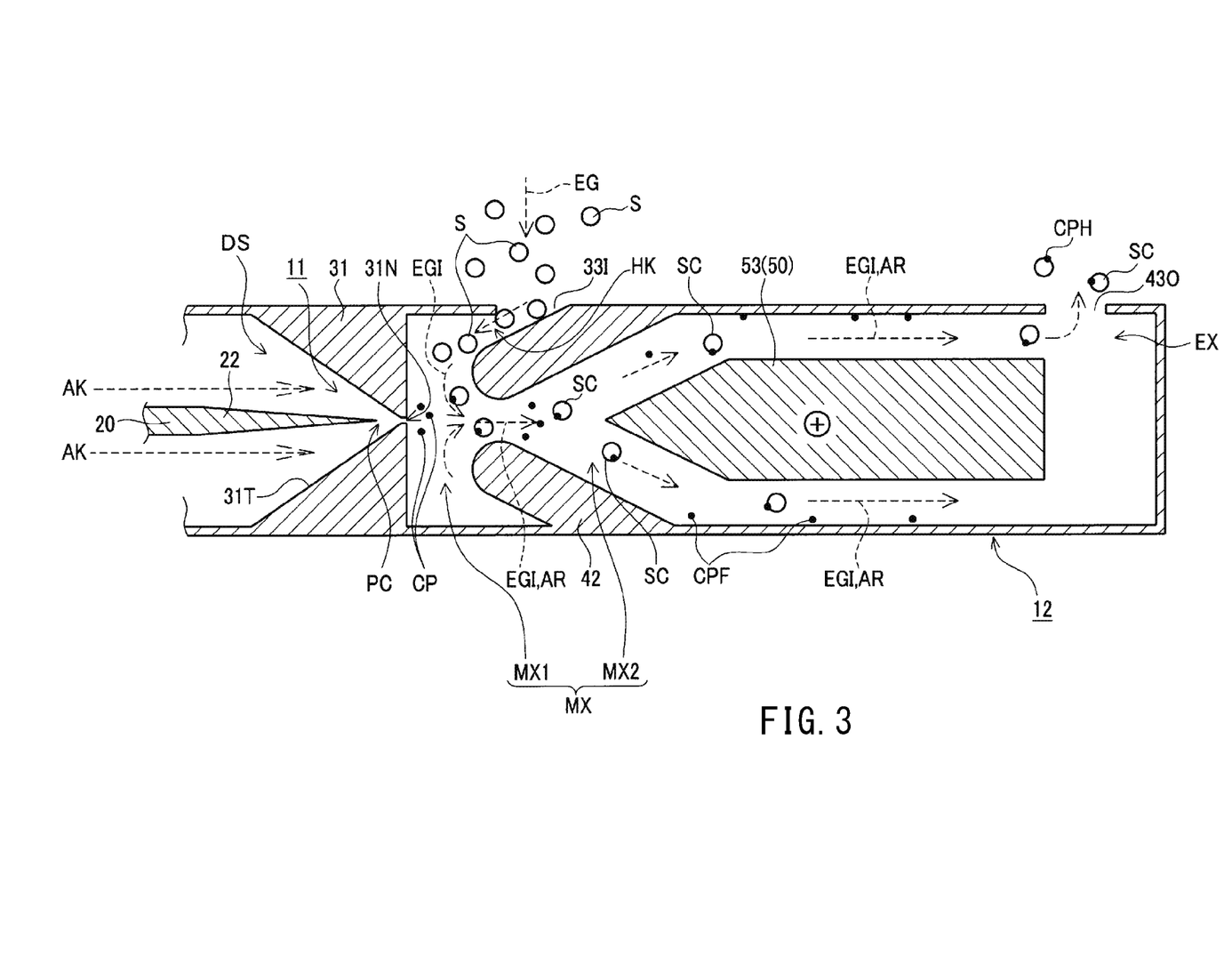
FIG. 3 Explanatory view schematically showing introduction of particulates into a particulate electrification section of the particulate detection system according to the embodiment, electrification of the particulates, and release of the electrified particulates from the particulate electrification section.

Of the space inside the particulate electrification section 12, the above-mentioned circular columnar space will be referred to as a "circular columnar mixing region MX1." Also, the slit-shaped internal space formed by the collection electrode 42 will be referred to as a "slit-shaped mixing region MX2" (see FIG. 3). The circular columnar mixing region MX1 and the slit-shaped mixing region MX2 will be collectively referred to as a "mixing region MX." Further, circular columnar space is also formed on the distal end side of the collection electrode 42, and serves as an exhaust passage EX which communicates with the exhaust port 430. In addition, on the proximal end side of the collection electrode 42, there is formed an introduction passage HK which extends from the intake port 331 to the mixing region MX (the circular columnar mixing region MX1).

Next, the electrical functions and operations of various sections of the particulate detection system 1 of the present embodiment will be described with reference to FIG. 3 in addition to FIG. 2. FIG. 3 schematically shows the electrical function and operation of the detection section 10 of the present system 1 in order to facilitate the understanding of the electrical function and operation.

The needlelike electrode member 20 is maintained at the second potential P72, which is a positive pulse voltage (1 to 2 kV0-p), which is obtained through half-wave rectification of a sinusoidal wave of 100 kHz, in relation to the first potential PV1 as described above. Meanwhile, the auxiliary electrode member 50 is maintained at the third potential PV3, which is a positive DC potential of 100 to 200 V in relation to the first potential PV1 as described above. Also, the first conduction member 13, the nozzle member 31, and the particulate electrification section 12 are maintained at the first potential P71. In addition, the housing member 14 is maintained at the ground potential PVE, which is the same as the potential of the ground input terminal 232 of the signal current detection circuit 230 and the potential of the exhaust pipe EP.

Accordingly, as described above, positive needle corona PC, which is corona around the needlelike distal end portion 22 serving as a positive electrode, is produced between the nozzle member 31 (the facing surface 31T) maintained at the first potential PV1 and the needlelike distal end portion 22 maintained at the second potential P72, which is a positive high potential in relation to the first potential PV1. As a result, $N_2$, $O_2$, etc. in the atmospheric air (air) thereround are ionized, whereby positive ions CP are produced. Some produced ions CP pass through the nozzle 31N and are jetted toward the mixing region MX, together with the air AR originating from the compressed air AK supplied to the discharge space DS. In the present embodiment, the needlelike distal end portion 22 and the nozzle member 31 surrounding the discharge space DS constitute the ion source 11 which generates ions CP by means of gaseous discharge (corona discharge) between the needlelike distal end portion 22 and the nozzle member 31.

When the air AR is jetted to the mixing region MX (the circular columnar mixing region MX1) through the nozzle 31N of the nozzle member 31, the air pressure in the circular columnar mixing region MX1 drops. Therefore, the exhaust gas EG is taken into the mixing region MX (the circular columnar mixing region MX1, the slit-shaped mixing region MX2) from the intake port 331 through the introduction passage HK. The introduced exhaust gas EGI is mixed with the air AR, and is discharged together with the air AR from the exhaust port 430 through the exhaust passage EX.

At that time, if particulates S such as soot are contained in the exhaust gas EG, as shown in FIG. 3, the particulates S are also introduced into the mixing region MX. Incidentally, the jetted air AR includes ions CP. Therefore, the ions CP adhere to the introduced particulates S such as soot, and the particulates S become positively electrified particulates SC. The positively electrified particulates SC are discharged, together with the introduced exhaust gas EGI and the air AR, from the exhaust port 430 through the mixing region MX and the exhaust passage EX.

Meanwhile, of the ions CP jetted to the mixing region MX, floating ions CPF not having adhered to the particulates S receive a repulsive force from the auxiliary electrode portion 53 of the auxiliary electrode member 50, and adhere to portions of the particulate electrification section 12, which is maintained at the first potential PV1 and which forms the collection electrode 42. As a result, the floating ions CPF are collected.

Next, there will be described the principle of detection of the particulates S in the present system 1. As shown in FIG. 2, when gaseous discharge occurs at the ion source 11, a discharge current Id is supplied to the needlelike distal end portion 22 from the second output terminal 212 of the ion source power supply circuit 210. The greater part of the discharge current Id flows to the nozzle member 31 (received current ij). This received current Ij flows through the first conduction member 13, and flows into first output terminal 211 of the ion source power supply circuit 210.

The greater part of the ions CP produced at the ion source 11 and jetted therefrom are collected by the collection electrode 42. A corrected current Ih originating from the charge carried by the floating ions CPF collected by the collection electrode 42 also flows into the first output terminal 211 through the first conduction member 13, which electrically communicates with the collection electrode 42 (the particulate electrification section 12). Namely, a received/collected current Ijh (=Ij+Ih) which is the sum of these currents flows through the first conduction member 13.

This received/collected current Ijh becomes slightly smaller in magnitude than the discharge current Id. This is because some of the ions CP produced at the ion source 11 adhere to the electrified particulates SC released from the exhaust port 430, whereby some of the ions CP are released from the exhaust port 430 (the released ions will be referred to as the "released ions CPH"). The received/collected current Ijh does not include a current component corresponding to the charge of the released ions CPH. Notably, the exhaust pipe EP through which the electrified particulates SC flow is maintained at the ground potential PVE.

Incidentally, when viewed from the ion source power supply circuit 210, an imbalance occurs between the discharge current Id flowing out from the second output terminal 212 and the received/collected current Ijh flowing into the first output terminal 211. Therefore, a signal current is corresponding to the shortage (the difference=discharge current−the received/collected current) flows from the ground potential PVE to the first output terminal 211, whereby a balanced state is created.

In view of this, in the present system 1, the signal current detection circuit 230—which has the signal input terminal 231 communicating with the first output terminal 211 and the ground input terminal 232 communicating with the ground potential PVE and which detects the signal current flowing between the signal input terminal 231 and the ground input terminal 232—is provided so as to detect the signal current Is which flows from the ground potential PVE to the signal current detection circuit 230 through the housing member 14 and the ground potential wiring line 167 of the cable 160, flows through the signal current detection circuit 230, and then flows to the first output terminal 211.

The magnitude of the signal current Is corresponding to the difference (the discharge current Id−the received/collected current Ijh) increases and decreases in accordance with the quantity of charge of the released ions CFH (ions adhering to the discharged, electrified particulates SC); accordingly, the quantity of particulates S in the introduced exhaust gas EGI; i.e., the quantity of particulates S contained in the exhaust gas EG flowing through the exhaust pipe EP. Accordingly, through detection of the signal current Is by the signal current detection circuit 230, there can be detected the quantity of particulates S contained in the exhaust gas EG, which corresponds to the signal current Is. Notably, in the present system 1, the converted value of the quantity of the particulates S is obtained from the detected signal current Is through conversion performed through use of a predetermined reference table.

Incidentally, as described above, the ion source power supply circuit 210 constitutes a constant current power source, and the discharge current Id (the gaseous discharge current in the present invention) supplied from the second output terminal 212 of the ion source power supply circuit 210 to the needlelike distal end portion 22 is feedback-controlled by the microprocessor 202 such that its rms value is maintained at a predetermined current value (for example, 5 µA (=target current It)).

Figure 5:
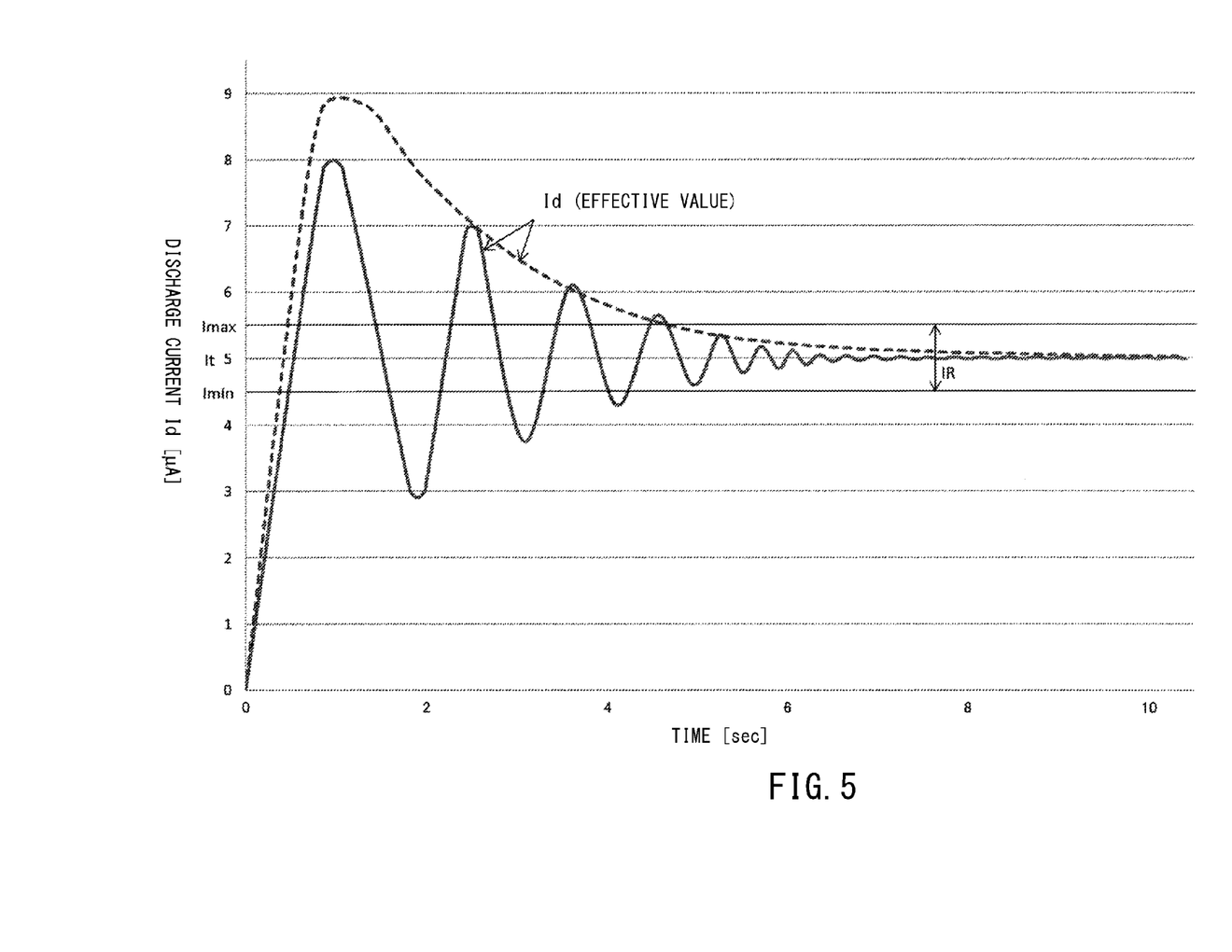
FIG. 5 Graph relating to the particulate detection system according to the embodiment and showing a change in discharge current with time after operation of an ion source is started.

In order to accurately detect the quantity of particulates S through use of the signal current Is, the discharge current Id subjected to the constant current control must be stable. However, in many cases, the discharge current Id is unstable immediately after the operation of the ion source 11 has been started by the ion source power supply circuit 210. Also, when the insulation properties of the ion source 11 has deteriorated due to adhesion of condensed water or soot to the circumference of the ion source 11, the discharge current Id repeats hunting or its initial value becomes excessively large as shown by a continuous line and a broken line in a graph shown in FIG. 5. In such a case, the discharge current Id takes a great deal of time to converge to the target current It. In such a state, the quantity of the ions CP generated by means of corona discharge varies. Therefore, if the signal current Is is detected by the signal current detection circuit 230 in the state in which the discharge current Id is unstable, difficulty is encountered in accurately detecting the quantity of the particulates S.

In view of the foregoing problem, the system 1 of the present embodiment has the heater 78 for heating the ion source 11 and the auxiliary electrode portion 53 of the auxiliary electrode member 50, and the heater energization circuit 226 for energizing the heater 78, as described above. After the operation of the ion source 11 has been started, the system 1 first causes the heater energization circuit 226 to perform low-temperature energization for a predetermined period by energizing the heater 78 by means of PWM control to thereby increase the temperature of the heater 78 to a heater temperature (100 to 200° C. in the present embodiment) for removing water (condensed water or the like) adhering to the ion source 11. In the case where the discharge current Id (gaseous discharge current) supplied from the ion source power supply circuit 210 has converged to the allowable range IR after elapse of the predetermined period, the system 1 stops the energization of the heater 78. Specifically, the allowable range IR is set for the target current It (=5 µA) of the discharge current Id such that the lower limit Imin of the range becomes 4.5 µA and the upper limit Imax of the range becomes 5.5 µA (see FIG. 5).

Meanwhile, in the case where the discharge current Id has not converged to the allowable range IR despite of elapse of the predetermined period, the system 1 causes the heater energization circuit 226 to perform high-temperature energization until the discharge current Id converges to the allowable range IR by changing the duty ratio of the PWM control performed by the heater energization circuit 226 (in other words, the value of the effective voltage applied to the heater 78 during the low-temperature energization) to thereby increase the temperature of the heater 78 to a heater temperature (600° C. in the present embodiment) for removing foreign substances (e.g., soot) which adhere to the ion source 11 and which cannot be removed by the low-temperature energization.

Namely, at the beginning, the heater 78 is energized by the low-temperature energization so as to increase the temperature of the heater 78 to a heater temperature at which water adhering to the ion source 11 is removed, to thereby heat the ion source 11. In the case where the discharge current Id has not converged to the allowable range IR despite of elapse of the predetermined period, the heater 78 is further energized by the high-temperature energization so as to increase the temperature of the heater 78 to a heater temperature at which foreign substances (e.g., soot) which cannot be removed by the low-temperature energization are removed, to thereby heat the ion source 1.

Subsequently, after the discharge current Id has converged to the allowable range IR, the system 1 stops the energization of the hater 78, and starts the detection of the quantity of the particulates S through use of the signal current is detected by the signal current detection circuit 230.

Next, of operations of the present system 1, an operation of the microprocessor 202 for executing a particulate detection routine will be described with reference to the flowcharts of FIGS. 6 through 8.

Figure 6:
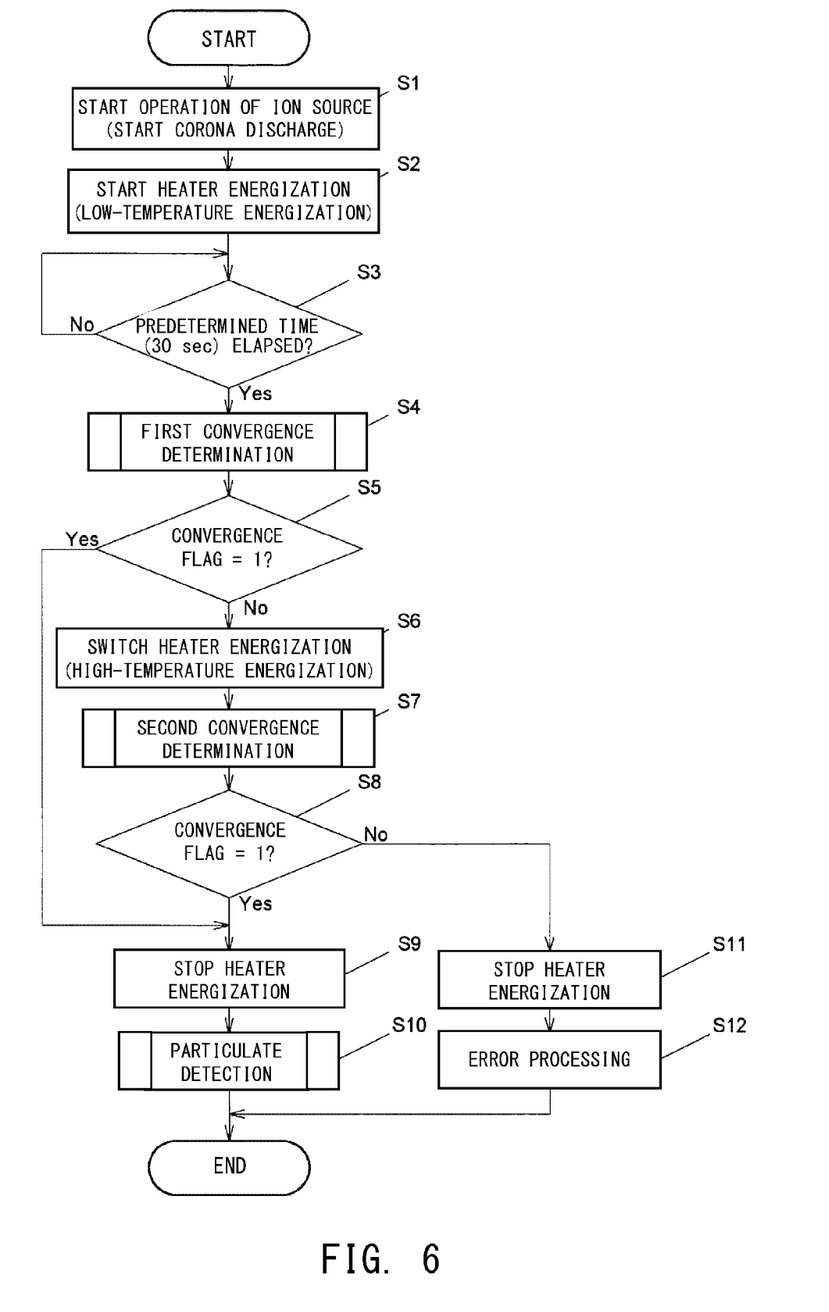
FIG. 6 Flowchart showing operation of the particulate detection system according to the embodiment.

First, in step S1 shown in FIG. 6, after performing necessary initial setting, the microprocessor 202 starts the operation of the ion source 11 by using the ion source power supply circuit 210. Notably, at that time, the microprocessor 202 separately performs constant current control for maintaining the discharge current Id at a fixed level. As a result, corona discharge is started.

In step S2 subsequent thereto, the microprocessor 202 causes the heater energization circuit 226 to perform the low-temperature energization by starting the energization of the heater 78 by means of PWM control to thereby increase the temperature of the heater 78 to a heater temperature (100 to 200° C.) at which water (condensed water or the like) adhering to the ion source 11 and the auxiliary electrode portion 53 of the auxiliary electrode member 50 is removed.

Next, in step S3, the microprocessor 202 determines whether or not a predetermined time (30 seconds in the present embodiment) has elapsed after the energization of the heater 78 had been started in step S2. In the case where the predetermined time has not yet elapsed (No), the microprocessor 202 repeats this step S3 until the predetermined time elapses. When the predetermined time has elapsed, the microprocessor 202 makes a "Yes" determination in step S3, and proceeds to step S4.

Figure 7:
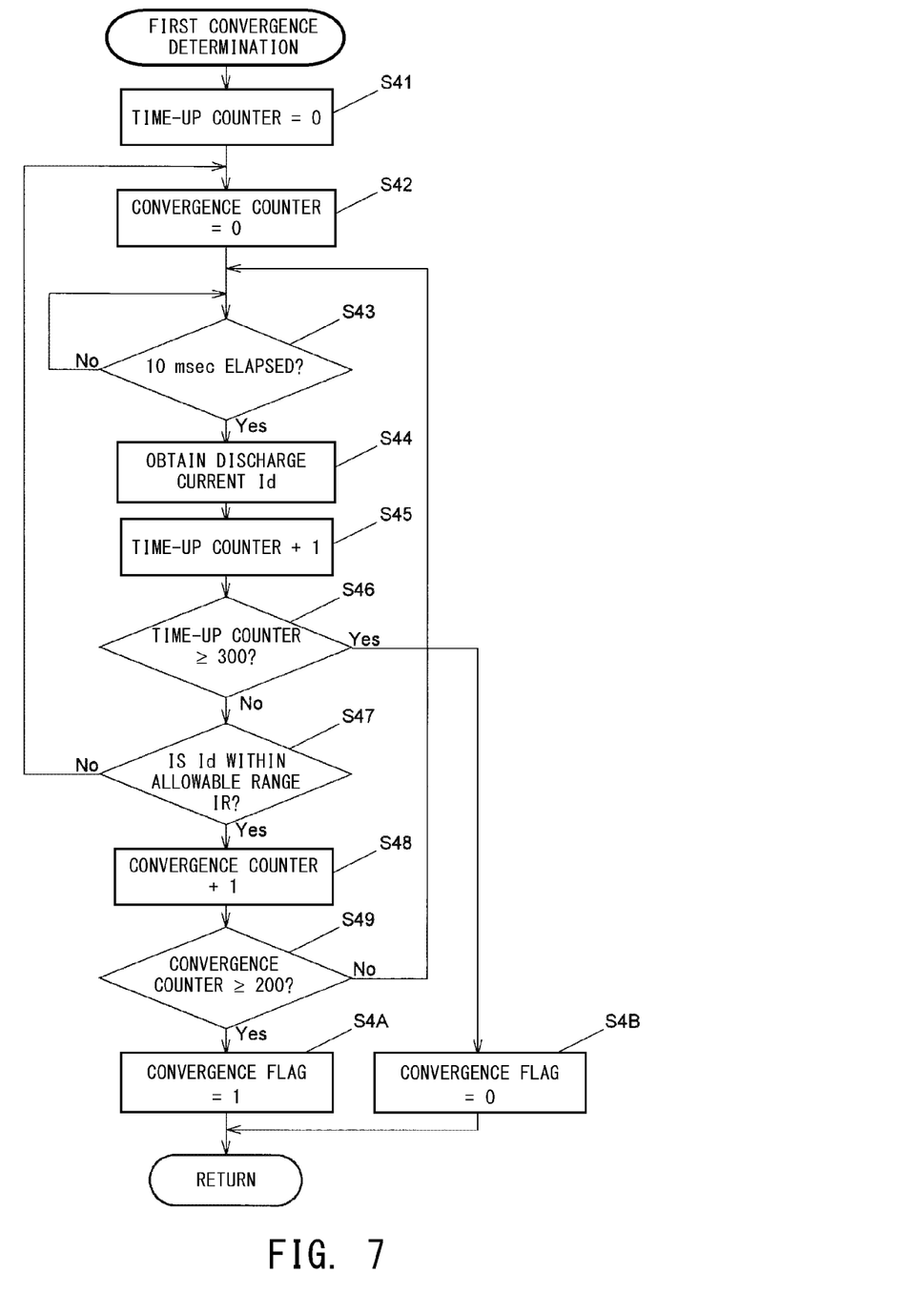
FIG. 7 Flowchart showing operation of a first convergence determination sub-routine according to the embodiment.

In step S4, the microprocessor 202 executes a first convergence determination sub-routine shown in FIG. 7 so as to determine, after elapse of the predetermined time, whether or not the discharge current Id supplied from the ion source power supply circuit 210 to the needlelike distal end portion 22 of the ion source 11 has converged to the allowable range IR (for example, Imin (=4.5 μA) to Imax (=5.5 μA)).

Next, the first convergence determination sub-routine of FIG. 7 will be described.

In step S41 shown in FIG. 7, the microprocessor 202 sets the value of a time-up counter to 0. This time-up counter is used for interrupting the determination of this first convergence determination sub-routine after elapse of 3 sec. In step S42 subsequent thereto, the microprocessor 202 sets the value of a convergence counter to 0. This convergence counter is used for determining whether or not the discharge current Id has converged to the allowable range IR.

Further, in step S43 subsequent thereto, the microprocessor 202 determines whether or not 10 msec has elapsed by using a timer which clocks 10 msec. In the case where 10 msec has not yet elapsed (No), the microprocessor 202 repeats this step S43. In the case where 10 msec has elapsed (Yes in step S43), the microprocessor 202 proceeds to step S44. As a result, every time 10 msec elapses, the processing of step S44 and steps subsequent thereto is executed.

In step S44, the microprocessor 202 obtains the value of the discharge current Id every time 10 msec elapses. In step S45 subsequent thereto, the microprocessor 202 increases the value of the time-up counter by one. Namely, the value of the time-up counter is increased by one every time 10 msec elapses.

Further, in step S46 subsequent thereto, the microprocessor 202 determines whether or not the value of the time-up counter becomes equal to or greater than 300; namely, whether or not 3 sec for interrupting the determination has elapsed after the start of this first convergence determination sub-routine. In the case where 3 sec has not yet elapsed (No in step S46), the microprocessor 202 proceeds to step S47.

In step S47, the microprocessor 202 determines whether or not the discharge current Id obtained in step S44 falls within the allowable range IR. In the case where the discharge current Id does not fall within the allowable range IR (No), the microprocessor 202 returns to step S42 and resets the value of the convergence counter to 0. Subsequently, after waiting for elapse of 10 msec in step S43, the microprocessor 202 again proceeds to step S44 so as to obtain the discharge current Id. Meanwhile, in the case where the microprocessor 202 determines in step S47 that the discharge current Id falls within the allowable range IR (Yes), the microprocessor 202 proceeds to step S48 so as to increase the value of the convergence counter by one, and then proceeds to step S49. In step S49, the microprocessor 202 determines whether or not the value of the convergence counter is equal to or greater than 200. In the case where the value of the convergence counter is not equal to or greater than 200 (No), the microprocessor 202 returns to step S43 while maintaining the value of the convergence counter. After that, the microprocessor 202 waits for elapse of 10 msec in this step S43, and again proceeds to step S44 so as to obtain the discharge current Id.

In the case where, during the repeated execution of steps S43 through S49, the value of the convergence counter reaches 200 before the value of the time up counter reaches 300; namely, in the case where the value of the discharge current Id continuously falls within the allowable range IR for 2 sec before elapse of the 3 sec for stopping the determination, the result of the determination in step S49 becomes "Yes," and the microprocessor 202 proceeds to step S4A. In step S4A, the microprocessor 202 determines that the discharge current Id has converged to the allowable range IR, and sets a convergence flag to 1. After that, the microprocessor 202 ends this first convergence determination sub-routine.

Meanwhile, in the case where, during the repeated execution of steps S42 through S47, the value of the time-up counter reaches 300 before the value of the convergence counter reaches 200, the result of the determination in step S46 becomes "Yes," and the microprocessor 202 proceeds to step S4B. In step S4B, the microprocessor 202 determines that the discharge current Id failed to converge to the allowable range IR, and sets a convergence flag to 0. After that, the microprocessor 202 ends this first convergence determination sub-routine.

Upon completion of the first convergence determination sub-routine of FIG. 7, the microprocessor 202 proceeds to step S5 of FIG. 6. In step S5, the microprocessor 202 determines whether or not the convergence flag is 1; namely, whether or not the discharge current Id has converged to the allowable range IR. In the case where the convergence flag is 1 (the discharge current Id has converged to the allowable range IR) (Yes), the microprocessor 202 proceeds to step S9 so as to cause the heater energization circuit 226 to stop the energization of the heater 78. Meanwhile, in the case where the microprocessor 202 determines in step S5 that the convergence flag is 0 (No); namely, the discharge current Id has not converged to the allowable range IR despite of elapse of the predetermined time (No), the microprocessor 202 proceeds to step S6.

In step S6, the microprocessor 202 causes the heater energization circuit 226 to perform the high-temperature energization by changing the duty ratio of the PWM control performed by the heater energization circuit 226 to thereby increase the temperature of the heater 78 to a heater temperature (600° C.) at which foreign substances (e.g., soot) which adhere to the ion source 11 and the auxiliary electrode portion 53 of the auxiliary electrode member 50 and which cannot be removed by the low-temperature energization are removed. In step S7 subsequent thereto, the microprocessor 202 executes a second convergence determination sub-routine shown in FIG. 8 so as to determine whether or not the discharge current Id has converged to the allowable range IR.

Next, the second convergence determination sub-routine of FIG. 8 will be described.

Figure 8:
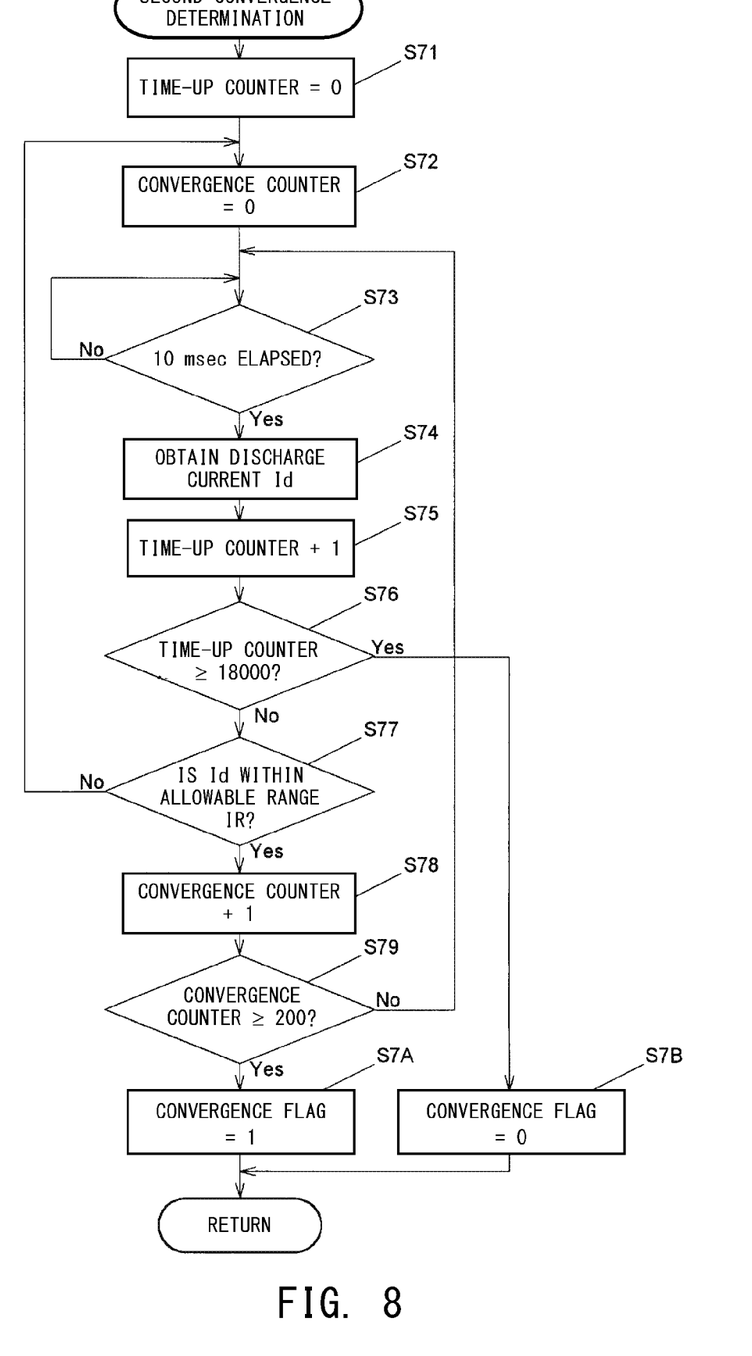
FIG. 8 Flowchart showing operation of a second convergence determination sub-routine according to the embodiment.

In step S71 shown in FIG. 8, the microprocessor 202 sets the value of a time-up counter to 0. This time-up counter is used for interrupting the determination of this second convergence determination sub-routine after elapse of 3 min. In step S72 subsequent thereto, the microprocessor 202 sets the value of a convergence counter to 0. This convergence counter is used for determining whether or not the discharge current Id has converged to the allowable range IR.

Further, in step S73 subsequent thereto, the microprocessor 202 determines whether or not 10 msec has elapsed by using a timer which clocks 10 msec. In the case where 10 msec has not yet elapsed (No), the microprocessor 202 repeats this step S73. In the case where 10 msec has elapsed (Yes in step S73), the microprocessor 202 proceeds to step S74. As a result, every time 10 msec elapses, the processing of step S74 and steps subsequent thereto is executed.

In step S74, the microprocessor 202 obtains the value of the discharge current Id every time 10 msec elapses. In step S75 subsequent thereto, the microprocessor 202 increases the value of the time-up counter by one. Namely, the value of the time-up counter is increased by one every time 10 msec elapses.

Further, in step S76 subsequent thereto, the microprocessor 202 determines whether or not the value of the time-up counter becomes equal to or greater than 18000; namely, whether or not 3 min (180 sec), which is the period for interrupting the determination, has elapsed after the start of this second convergence determination sub-routine. In the case where 3 min has not yet elapsed (No in step S76), the microprocessor 202 proceeds to step S77.

In step S77, the microprocessor 202 determines whether or not the discharge current Id obtained in step S74 falls within the allowable range IR. In the case where the discharge current Id does not fall within the allowable range IR (No), the microprocessor 202 returns to step S72 and resets the value of the convergence counter to 0. Subsequently, after waiting for elapse of 10 msec in step S73, the microprocessor 202 again proceeds to step S74 so as to obtain the discharge current Id. Meanwhile, in the case where the microprocessor 202 determines in step S77 that the discharge current Id falls within the allowable range IR (Yes), the microprocessor 202 proceeds to step S78 so as to increase the value of the convergence counter by one, and then proceeds to step S79. In step S79, the microprocessor 202 determines whether or not the value of the convergence counter is equal to or greater than 200. In the case where the value of the convergence counter is not equal to or greater than 200 (No), the microprocessor 202 returns to step S73 while maintaining the value of the convergence counter. After that, the microprocessor 202 waits for elapse of 10 msec in this step S73, and again proceeds to step S74 so as to obtain the discharge current Id.

In the case where the value of the convergence counter reaches 200 during the repeated execution of steps S73 through S79; namely, in the case where the value of the discharge current Id continuously falls within the allowable range IR for 2 sec, the result of the determination in step S79 becomes "Yes," and the microprocessor 202 proceeds to step S7A. In step S7A, the microprocessor 202 determines that the discharge current Id has converged to the allowable range IR, and sets the convergence flag to 1. After that, the microprocessor 202 ends this second convergence determination sub-routine.

Meanwhile, in the case where, during the repeated execution of steps S72 through S77, the value of the time-up counter reaches 18000 before the value of the convergence counter reaches 200, the result of the determination in step S76 becomes "Yes," and the microprocessor 202 proceeds to step S7B. In step S7B, the microprocessor 202 sets the convergence flag to 0. After that, the microprocessor 202 ends this second convergence determination sub-routine. In this case, the discharge current Id failed to converge to the allowable range IR within 3 min.

Upon completion of the second convergence determination sub-routine of FIG. 8, the microprocessor 202 proceeds to step S8 of FIG. 6.

In step S8, the microprocessor 202 determines whether or not the convergence flag is 1; namely, whether or not the discharge current Id has converged to the allowable range IR. In the case where the convergence flag is 1 (the discharge current Id has converged to the allowable range IR) (Yes), the microprocessor 202 proceeds to step S9. In step S9, the microprocessor 202 causes the heater energization circuit 226 to stop the energization of the heater 78. After that, the microprocessor 202 proceeds to step S10, and starts the detection of the quantity of the particulates S through use of the signal current Is.

Meanwhile, in the case where the microprocessor 202 determines in step S8 that the convergence flag is 0 (No); namely, in the case where it is determined by the second convergence determination sub-routine that the discharge current Id failed to converge to the allowable range IR within 3 min, the microprocessor 202 proceeds to step S11. In step S11, the microprocessor 202 causes the heater energization circuit 226 to stop the energization of the heater 78. In step S12 subsequent thereto, the microprocessor 202 performs error processing necessary for interrupting the processing. In this case, the microprocessor 202 ends the particulate detection routine without performing the particulate detection.

As described above, the system 1 of the present embodiment has the heater 78 for heating the ion source 11 and the heater energization circuit 226 for energizing the heater 78. After the operation of the ion source 11 has been started in step S1, the system 1 first causes the heater energization circuit 226 to perform low-temperature energization for a predetermined period (30 seconds in the present embodiment) to thereby increase the temperature of the heater 78 to a heater temperature at which water adhering to the ion source 11 is removed (steps S2 through S3).

In the case where the discharge current Id has not converged to the allowable range IR despite of elapse of the predetermined period (No in step S5), the system 1 causes the heater energization circuit 226 to perform the high-temperature energization until the discharge current Id converges to the allowable range IR (steps S7 to S8) to thereby increase the temperature of the heater 78 to a heater temperature at which foreign substances (e.g., soot) which adhere to the ion source 11 and which cannot be removed by the low-temperature energization are removed (step S6).

Namely, at the beginning, the heater 78 is energized by the low-temperature energization so as to remove water adhering to the ion source 11. However, in the case where the discharge current Id has not converged to the allowable range IR despite of elapse of the predetermined period, the heater 78 is further energized by the high-temperature energization so as to remove foreign substances (e.g., soot) adhering to the ion source 11.

Therefore, in the present system 1, the amount of current consumed as a result of the energization of the heater 78 at the beginning can be reduced by the low-temperature energization. In addition, when necessary, foreign substances are removed by the high-temperature energization, whereby the gaseous discharge current can be caused to converge to the allowable range IR.

Since the detection of the quantity of the particulates S through use of the signal current Is is started in a state in which the discharge current Id is stable (step S10), the detection is not performed in a state in which the detection accuracy has dropped. Therefore, the quantity of the generated ions CP becomes stable, and the quantity of the particulates S can be detected accurately. Also, it is possible to remove water droplets (e.g., droplets of condensed water) and foreign substances (e.g., soot), which adhere to the circumference of the ion source 11, to thereby recover the insulation properties of the ion source 11. Thus, the discharge current Id can be quickly converged to the allowable range IR, whereby the time required to start the detection of the quantity of the particulates S can be shortened.

Further, in the system 1 of the present embodiment, the auxiliary electrode member 50 has the auxiliary electrode portion 53 which is provided at a distal end portion thereof and which serves as an auxiliary electrode, and the heater 78 heats the auxiliary electrode portion 53 of the auxiliary electrode member 50 in addition to the ion source 11. By virtue of this, it is possible to recover the insulation properties of the auxiliary electrode portion 53 having deteriorated as a result of adhesion of foreign substances, such as condensed water and soot, to the auxiliary electrode portion 53 serving as an auxiliary electrode. Therefore, the quantity of the particulates S can be detected more properly.

In the present embodiment, the signal current is corresponds to the signal corresponding to the quantity of electrified particulates SC in the present embodiment. Also, the signal current detection circuit 230 of the measurement control circuit 220 which detects the signal current Is corresponds to the detection circuit of the present invention, and the signal current detection circuit 230 and the microprocessor 202 corresponds to the control section of the present invention. Also, the ion source power supply circuit 210 corresponds to the drive circuit and the ion source drive circuit of the present invention, and the auxiliary electrode power supply circuit 240 corresponds to the drive circuit and the auxiliary electrode drive circuit of the present invention.

Further, the microprocessor 202 which executes steps S2 to S3 corresponds to the first heater energization control means of the present invention, and the microprocessor 202 which executes step S6 corresponds to the second heater energization start means of the present invention.

Also, the microprocessor 202 which executes steps S4 to S5 and steps S7 to S8 corresponds to the current convergence determination means of the present invention, and the microprocessor 202 which executes step S10 corresponds to the detection start means of the present invention.

In the above, the present invention has been described on the basis of the system 1 of the embodiment. However, the present invention is not limited to the above-described embodiment, and may be modified freely without departing from the scope of the invention.

For example, in the embodiment, the heater-equipped auxiliary electrode insulating pipe 79 in which the heater 78 is integrally formed on the surface of the auxiliary electrode insulating pipe 77 covering the circumference of the extending portion 51 of the auxiliary electrode member 50 is provided, and the ion source 11 and the auxiliary electrode portion 53 of the auxiliary electrode member 50 are heated by the heater 78 of the heater-equipped auxiliary electrode insulating pipe 79. However, the form of the heater is not limited thereto, and a heater for heating the ion source 11 only may be provided. Also, there may be provided two heaters for separately heating the ion source 11 and the auxiliary electrode portion 53 of the auxiliary electrode member 50.

Also, in the embodiment, in step S9, the heater energization circuit 226 is caused to stop the energization of the heater 78. However, the embodiment may be modified to decrease the duty ratio of PWM control in step S9 so as to supply a small amount of electric power to the heater 78, to thereby continue slight heat generation.

Also, in the embodiment, the signal current Is is converted to the quantity of the particulates S through use of a predetermined reference table. However, the signal current Is may be converted to the quantity of the particulates S through use of a predetermined conversion equation. Also, the magnitude of the signal current is itself may be used as a physical quantity corresponding to the quantity of the particulates S. Further, in the embodiment, the needlelike electrode member 20 is disposed in the discharge space DS. However, the embodiment may be modified in such a manner that the needlelike distal end portion 22 of the needlelike electrode member 20 is disposed to face the mixing area MX, gaseous discharge is produced between the needlelike distal end portion 22 and the inner surface of the particulate electrification section 12 forming the mixing area MX.

DESCRIPTION OF SYMBOLS

AM: car (vehicle)
ENG: engine (internal combustion engine)
EP: exhaust pipe (gas flow pipe)
EG: exhaust gas
EGI: introduced exhaust gas
S: particulates
SC: electrified particulates
CP: ions
CPF: floating ions
CPH: released ions
Id: discharge current (gaseous discharge current)
Is: signal current
1: particulate detection system
10: detection section
11: ion source
12: particulate electrification section
20: needlelike electrode member
22: needlelike distal end portion (of the needlelike electrode member) (ion source)
31: nozzle member (ion source)
42: collection electrode
50: auxiliary electrode member
53: auxiliary electrode portion (of the auxiliary electrode member) (auxiliary electrode)
78: heater
202: microprocessor (control section)
201: circuit section
210: ion source power supply circuit (drive circuit, ion source drive circuit)
220: measurement control circuit
226: heater energization circuit
230: signal current detection circuit (control section, detection circuit)
240: auxiliary electrode power supply circuit (drive circuit, auxiliary electrode drive circuit)
It: target current
IR: allowable range
S2 to S3: first heater energization start means
S6: second heater energization control means
S4 to S5, S7 to S8: current convergence determination means
S10: detection start means

The invention claimed is:

1. A particulate detection system for detecting the quantity of particulates contained in a gas under measurement flowing through a gas flow pipe, comprising:
   a detection section attached to the gas flow pipe;
   a drive circuit for driving the detection section; and
   a control section for controlling the drive circuit and detecting the quantity of the particulates,
   wherein the detection section includes:
      an ion source for generating ions by means of gaseous discharge,
      a particulate electrification section for mixing a portion of the gas under measurement with the ions to thereby produce electrified particulates which originate from the particulates within the gas under measurement and which carry the ions adhering thereto, and
      a heater for heating the ion source;
   wherein the drive circuit includes:

an ion source drive circuit for performing constant current control such that the gaseous discharge current supplied to the ion source becomes equal to a predetermined target current, and a heater energization circuit for energizing the heater; and wherein the control section includes:

a detection circuit for detecting a signal corresponding to the quantity of the electrified particulates, and a processor configured to execute instructions configured to:

cause the heater energization circuit to perform low-temperature energization for a predetermined period after operation of the ion source by the ion source drive circuit has been started, to thereby increase the temperature of the heater to a heater temperature at which water adhering to the ion source is removed, determine, after elapse of the predetermined period, whether or not the gaseous discharge current supplied from the ion source drive circuit has converged to a predetermined allowable range including the target current, when it is determined that the gaseous discharge current has not yet converged, cause the heater energization circuit to perform high-temperature energization until the gaseous discharge current converges to the predetermined allowable range, to thereby increase the temperature of the heater to a heater temperature at which a foreign substance which adheres to the ion source and cannot be removed by the low-temperature energization is removed, and start detection of the quantity of the particulates through use of the signal after the gaseous discharge current has converged to the allowable range.

2. A particulate detection system according to claim 1, wherein the detection section includes a collection electrode for collecting floating ions which are a portion of the ions and which failed to adhere to the particulates when the ions was mixed with the gas under measurement, and an auxiliary electrode for assisting the collection of the floating ions by the collection electrode;

the drive circuit includes an auxiliary electrode drive circuit for driving the auxiliary electrode; and the heater is configured to heat the auxiliary electrode in addition to the ion source.

\* \* \* \* \*